(12) United States Patent
Pebay et al.

(10) Patent No.: US 11,149,245 B2
(45) Date of Patent: Oct. 19, 2021

(54) AUTOMATED SYSTEM FOR MAINTENANCE AND DIFFERENTIATION OF PLURIPOTENT STEM CELLS

(71) Applicant: Tecan Trading AG, Männedorf (CH)

(72) Inventors: Alice Pebay, East Melbourne (AU); Alex Hewitt, East Melbourne (AU); Duncan Crombie, East Melbourne (AU); Helena Liang, East Melbourne (AU); Raymond Wong, East Melbourne (AU); Maciej Daniszewski, East Melbourne (AU); Marco Zalivani, Männedorf (CH)

(73) Assignee: Tecan Trading AG, Männedorf (CH)

( * ) Notice: Subject to any disclaimer, the term of this patent is extended or adjusted under 35 U.S.C. 154(b) by 322 days.

(21) Appl. No.: 15/478,585

(22) Filed: Apr. 4, 2017

(65) Prior Publication Data

US 2018/0282682 A1 Oct. 4, 2018

(51) Int. Cl.
| | |
|---|---|
| *C12M 1/36* | (2006.01) |
| *C12M 1/26* | (2006.01) |
| *C12M 1/12* | (2006.01) |
| *C12M 3/06* | (2006.01) |
| *C12M 3/04* | (2006.01) |
| *C12M 1/00* | (2006.01) |

(52) U.S. Cl.
CPC .......... *C12M 41/48* (2013.01); *C12M 23/20* (2013.01); *C12M 23/28* (2013.01); *C12M 23/50* (2013.01); *C12M 27/10* (2013.01); *C12M 27/16* (2013.01); *C12M 29/14* (2013.01); *C12M 33/04* (2013.01); *C12M 37/00* (2013.01); *C12M 41/14* (2013.01); *C12M 47/02* (2013.01)

(58) Field of Classification Search
CPC .............................. C12M 41/14; C12M 41/48
See application file for complete search history.

(56) References Cited

U.S. PATENT DOCUMENTS

| | | | | |
|---|---|---|---|---|
| 2003/0040104 | A1* | 2/2003 | Barbera-Guillem | ... C12M 23/24 435/286.2 |
| 2004/0050866 | A1* | 3/2004 | Ingenhoven | .......... B01L 3/0241 222/135 |
| 2006/0257999 | A1* | 11/2006 | Chang | ................. B01J 19/0046 435/289.1 |
| 2006/0275888 | A1* | 12/2006 | Hibino | .................. C12M 23/50 435/286.2 |
| 2012/0195811 | A1* | 8/2012 | Nelson | ............... G01N 35/0099 422/522 |
| 2016/0177244 | A1* | 6/2016 | Conway | ................. C12M 23/12 435/377 |

(Continued)

OTHER PUBLICATIONS

Crombie, et al., "Development of a Modular Automated System for Maintenance and Differentiation of Adherent Human Pluripotent Stem Cells", preprint first posted on line Oct. 5, 2016, 20 pages.

(Continued)

*Primary Examiner* — William H. Beisner
(74) *Attorney, Agent, or Firm* — Hovey Williams LLP

(57) ABSTRACT

The present invention relates to the automated maintenance of cells particularly reprogrammed somatic cells into iPSCs to enable the large-scale culture and passaging of human pluripotent stem cells (PSCs) that can be adapted to a Freedom EVO®.

44 Claims, 5 Drawing Sheets

(56) References Cited

U.S. PATENT DOCUMENTS

2018/0135002 A1* 5/2018 Kato .................. C12M 27/16

OTHER PUBLICATIONS

Crombie, et al., "Development of a Modular Automated System for Maintenance and Differentiation of Adherent Human Pluripotent Stem Cells", Jan. 25, 2017, SLAS Discovery, pp. 1-10.
Hussain, et al., "Reproducible culture and differentiation of mouse embryonic stem cells using an automated microwell platform", 2013, Biochemical Engineering Journal, vol. 77, pp. 246-257.
Tecan Journal, "Seeing More Clearly", Tecan Journal Feb. 2016, pp. 8-9.
Sevilla, et al., "Automated, high-throughput derivation, characterization and differentiation of induced pluripotent stem cells", Nature Methods, Aug. 2015, 14 pages.
Tecan, "Cell Maintenance—Fibroblasts and stem cells are cultivated in RoboFlasks and collected in Falcon Tubes", Cell Biology, 5 pages.

* cited by examiner

AUTOMATED SYSTEM FOR MAINTENANCE AND DIFFERENTIATION OF PLURIPOTENT STEM CELLS

FIELD OF THE INVENTION

The present invention provides an automated system for sterilely maintaining, passaging and differentiating cells, particularly stem cells and most particularly induced pluripotent stem cells (iPSCs). In particular the system enables large-scale sterile culture and passaging of human pluripotent stem cells (PSCs) using a customized Freedom EVO® (Tecan Switzerland AG). Key advantages of this automated approach are the ability to increase sample size, reduce variability during reprogramming or differentiation, and enable medium to high-throughput analysis of human PSCs and derivatives.

BACKGROUND OF THE INVENTION

Advances in technology have enabled the reprogramming of adult somatic cells into human iPSCs[1-3] which can be subsequently differentiated into cells of interest, providing a potentially inexhaustible supply of cells with disease-specific genotypes and phenotypes. Patient-specific iPSCs have tremendous potential for development of regenerative medicine, disease modelling and drug discovery. However, the processes of reprogramming, maintenance and differentiation are labour intensive and subject to inter-technician variability.

A main bottleneck in using iPSCs for disease modelling lies in the vast amount of time and manpower necessary to maintain cells in culture, making large-scale population studies almost unfeasible within the constraints of an average sized laboratory. The use of robotics could enable this type of research. A key advantage of an automated approach is the ability to increase sample size and reduce variability during the reprogramming, maintenance and differentiation of iPSCs. Current applications of automated technology for stem cell research are still limited. Among the very few systems reported for automation of stem cell culture and differentiation are the Automation Partnership Biosystems (TAP Biosystems), which has already been used to maintain human mesenchymal stem cells[4] as well as human bone marrow-derived cells[5]; and the AutoCulture® system (Kawasaki Heavy Industries), which has been used to maintain human cardiac stem cells[6]. Additionally, prototypes have been developed to change medium for cell culture of embryonic stem cells[7].

The laboratory automation platform Freedom EVO® (Tecan Switzerland AG)) has been adapted to maintain mouse embryonic stem cells and differentiate them towards a neuronal lineage[8]. Similarly, a few groups have reported on the reprogramming, maintenance and differentiation of human PSCs on automated laboratory automation platforms. The New York Stem Cell Foundation uses a self-designed robotic platform comprised of three platforms using STAR liquid handling systems (Hamilton Robotics) to carry-out the maintenance and passaging of human iPSCs[9]. Another automated platform was described for the maintenance of human iPSCs, using a robotic arm (MELFA, RV-4FC-D, Mitsubishi) for liquid handling[10]. A smaller liquid handler was recently described for the maintenance and passaging of human PSCs, based on a self-contained Gilson's pipette Max liquid handler that can process up to 96 well plates[11]. However, these systems require additional offline steps as there is no associated incubator and many steps require human contribution thereby introducing further opportunities for loss of sterility and inter-technician variability.

A system is required for an automated laboratory automation platform to enable the ability to maintain large numbers of cells such as iPSC lines or progeny, with minimal variation for subsequent use in modelling complex diseases, such as age-related macular degeneration, primary open angle glaucoma or dementias etc., as well as therapeutic compound screening.

SUMMARY OF THE INVENTION

The present invention provides an automated system for maintaining, passaging and differentiating cells, particularly stem cells and most particularly induced pluripotent stem cells (iPSCs).

Accordingly, in an aspect of the present invention there is provided an automated system for sterile cell culture, said system comprising:
  a platform for receiving and moving a cell culture plate from a housing;
  a manipulator arm for moving the culture plate between the housing and the platform and placing the culture plate on the platform;
  a receptacle for containing a sterile solution to be dispensed controllably and sterilely to the culture plate;
  a disposable tip carrier for providing sterile disposable tips for dispensing the solution from the receptacle to the culture plate and removing solution from the culture plate;
  a liquid handling system which interacts with the disposable tip carrier and disposable tips and the receptacle to controllably and sterilely dispense to and remove solution from the culture plate such that the solution is sterilely dispensed without dispersion outside the stem cell culture and removed at a predetermined volume; and
  a controlling system to automate and program any one of the manipulator arm, the platform and the liquid handling system such that the liquid handling system controllably and sterilely delivers and removes predetermined aliquots of solution to and from the culture plate before the manipulator arm optionally returns the culture plate to the housing.

In yet another aspect of the invention there is provided an automated system for sterile passaging of cells, said system comprising:
  a platform for receiving and moving a cell culture plate from a housing;
  a manipulator arm for moving the culture plate between the housing and the platform and placing the culture plate on the platform;
  a receptacle for containing a sterile solution or a cell releasing solution to be dispensed controllably and sterilely to the culture plate;
  a disposable tip carrier for providing sterile disposable tips for dispensing the solution or the cell releasing solution from the receptacle to the culture plate;
  a liquid handling system which interacts with the disposable tip carrier and disposable tips, and the receptacle to controllably and sterilely dispense to and remove solution and the cell releasing solution from the culture plate such that the solution or cell releasing solution is controllably and sterilely dispensed without dispersion outside the stem cell culture and removed at a predetermined volume; and a controlling system to automate and program any one of the manipulator arm, the platform, and the liquid handling system such that the liquid handling system controllably and sterilely delivers and removes predetermined aliquots of solution and cell releasing solution to and from the culture plate sufficient to detach the cells from the culture plate for further passaging.

In another aspect of the present invention, there is provided an automated system for sterile differentiation of cells, said system comprising a platform for receiving and moving a cell culture plate from a housing;

a manipulator arm for moving the culture plate between the housing and the platform and placing the culture plate on the platform;

a receptacle for containing a sterile solution or a differentiation factor to be dispensed controllably and sterilely to the culture plate;

a disposable tip carrier for providing sterile disposable tips for dispensing the solution or the differentiation factor from the receptacle to the culture plate;

a liquid handling system which interacts with the disposable tip carrier and disposable tips and the receptacle to controllably and sterilely dispense to the culture plate such that the solution and differentiation factor are controllably and sterilely dispensed without dispersion outside the stem cell culture and removed at a predetermined volume; and a controlling system to automate and program any one of the manipulator arm, the platform, and the liquid handling system such that the liquid handling system controllably and sterilely delivers and optionally removes predetermined aliquots of solution or differentiation factor to and from the culture plate before the manipulator arm optionally returns the culture plate to the housing.

In yet another aspect of the invention there is provided an automated method for sterile cell culture, said method comprising culturing cells in the automated system of the present invention.

In another aspect of the present invention there is provided an automated method for sterile passaging of cells said method comprising passaging the cells in the automated system of the present invention.

In a further aspect of the present invention there is provided an automated method for sterile differentiating of cells, said method comprising differentiating cells in the automated system of the present invention.

DETAILED DESCRIPTION OF THE INVENTION

Figure 1A:
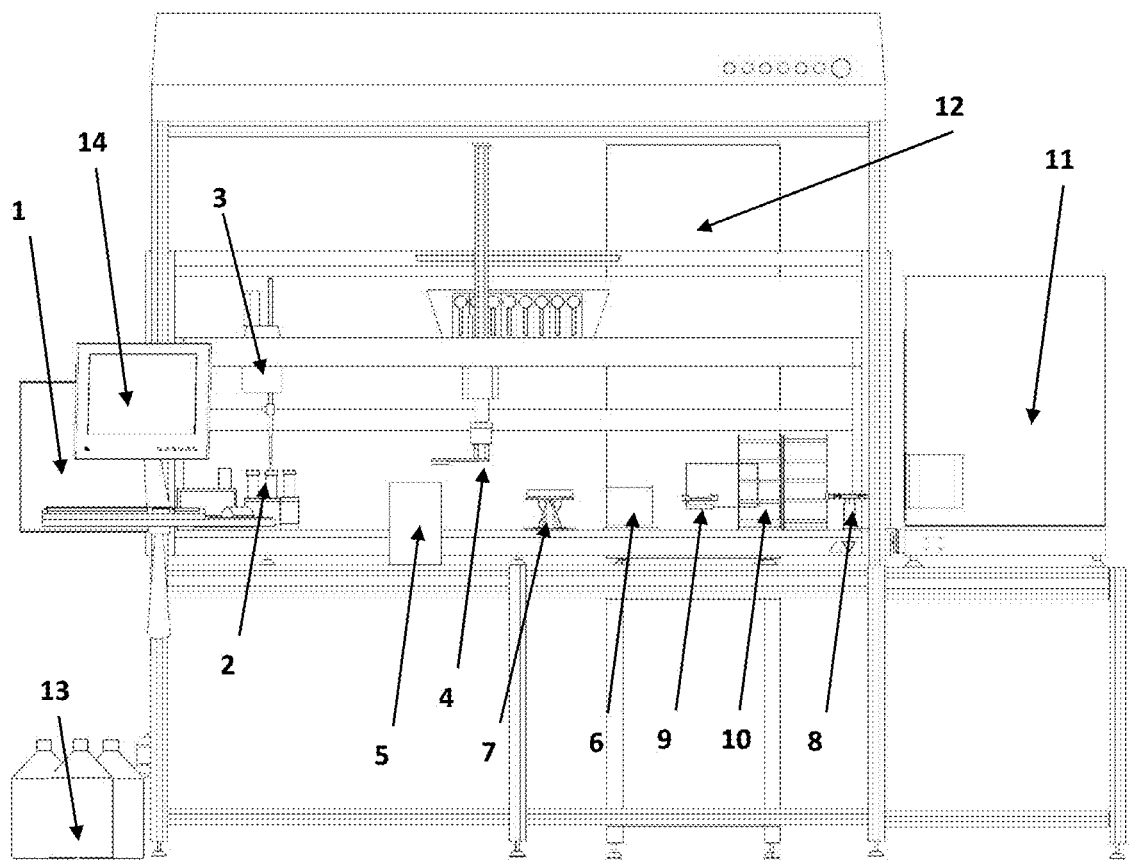
FIG. 1A shows Computer Aided Design (CAD) images of the laboratory automation platform from front, (1) cabinet with medium bottle and pump; (2) carriers for tubes; (3) robotic liquid handling arm; (4) manipulator arm; (5) waste for disposable tips and carriers for disposable tips; (6) carrier for 5 mL disposable tips; (7) tilting carrier with platforms; (8) transfer station for carriers for 5 mL disposable tips; (9) transfer station to the Liconic incubator; (10) hotel; (11) carousel for disposable tip carriers, (12) incubator; (13) autoclaved system liquid containers; (14) computer.

Culturing, maintaining and differentiating large numbers of cells is labour intensive and subject to inter-technician variability. An automated approach has the ability to increase sample size and reduce variability during the reprogramming, maintenance and differentiation of the cells.

Accordingly, in an aspect of the present invention there is provided an automated system for sterile cell culture, said system comprising:

a platform for receiving and moving a cell culture plate from a housing;

a manipulator arm for moving the culture plate between the housing and the platform and placing the culture plate on the platform;

a receptacle for containing a sterile solution to be dispensed controllably and sterilely to the culture plate;

a disposable tip carrier for providing sterile disposable tips for dispensing the solution from the receptacle to the culture plate;

a liquid handling system which interacts with the disposable tip carrier and the receptacle to controllably and sterilely dispense to and remove solution from the culture plate such that the solution is sterilely dispensed without dispersion outside the stem cell culture and removed at a predetermined volume; and a controlling system to automate and program any one of the manipulator arm, the platform and the liquid handling system such that the liquid handling system controllably and sterilely dispenses and removes individual aliquots of medium to and from the culture plate before the manipulator arm optionally returns the culture plate to the housing.

Protocols to allow for the automated maintenance of cells have been established by the present invention which enables large-scale sterile culture and passaging of cells such as the human pluripotent stem cells (PSCs) and adapting the automated system to a system such as the Freedom EVO®. Key advantages of this automated approach are the ability to sterilely increase sample size, reduce variability during reprogramming or differentiation, and enable medium to high-throughput analysis of cells such as human PSCs and derivatives. These techniques will become increasingly important with the emergence of clinical trials using stem cells.

The present invention relates to cell culture. This includes the process of maintaining the cells. The term "maintaining" or "maintain", as used herein, refers to all processes that will keep the cells alive and in culture. For instance, maintain will include changing media, rinsing cells, coating plates to enhance cell growth, passaging the cells and differentiating the cells. A person skilled in the art would be familiar with these processes that are necessary for keeping the cells alive in culture.

The automated system of the present invention will comprise a number of components that are necessary to automate cell culture. The system may comprise at least a platform, a manipulator arm, housing, a receptacle, a disposable tip carrier, a liquid handling system and a controlling system. These interact together to provide an automated sterile cell culture. In a preferred embodiment, the automated system comprises a laboratory automated platform such as but not limited to a Freedom Evo® which is further adapted for further automation to provide an automated laboratory automated platform.

The automated system of the present invention is applicable for use in the maintenance of any cells in culture that require regular maintenance such as, but not limited to medium changing and passaging. Preferably, the cells are somatic cells and more preferably the cells are reprogrammed cells.

Advances in technology have enabled the reprogramming of adult somatic cells into human induced pluripotent stem cells (iPSCs)[1-3], which can be subsequently differentiated into cells of interest, providing a potentially inexhaustible supply of cells with disease-specific genotypes and phenotypes. Ideally, generation of iPSCs may be performed by nucleofection. However, there are any numbers of techniques available to the skilled addressee that may be applied to reprogram somatic cells to iPSCs. For instance, reprogramming may be performed by any one of, but not limited to nucleofection of episomal factors, viral delivery (integrating and non integrating), or RNA delivery.

The automated system described herein, may also be used to reprogram the somatic cells. The system may be adapted to prepare the cells and perform any method available to the skilled addressee such as, but not limited to nucleofection of episomal factors, viral delivery (integrating and non integrating), or RNA delivery which requires delivery of factors from individual receptacles containing the factors to a somatic cell culture on the platform.

Alternatively, the reprogramming may be conducted offline and the reprogrammed cells maintained using the automated system.

In a preferred embodiment, the automated system of the present invention is for use in maintaining reprogrammed somatic cells, more preferably, iPSCs.

The cells of the present invention are maintained in culture in sterile conditions. Due to the nature of the automated system, it is generally applicable to use a culture plate. Any size plate may be used, providing it can be placed on the platform and that the manipulator arm can access the plate from the housing to place it on the platform. Also, it is desirable that the plate is accessible and compatible to the liquid handling system such that the liquid handling system can deliver to and remove solution from the culture plate to enable the maintenance of the cells. Applicants have found that 6 culture well plates (ANSI microplate standard footprint) are useful for the automated system. However, any plates can be used providing the necessary interactions between the manipulator arm, the liquid handling system and the disposable tip carrier are achieved.

The culture plates are removed from a housing. In one embodiment the housing is an incubator or a hotel to hold the culture plate for later use. Either the incubator or the hotel is integrated and seamless within the automated system or they may exist as separate modular units that can be added to the automated system. The hotel is used to hold the culture plates before placing them into the incubator or before they receive passaged cells. The use of a hotel is convenient to reduce the clutter on the work bench when processing a large number of cell culture plates.

In another embodiment the incubator or the hotel are integrated within the automated system such that a manipulator arm can automatically access the housing or the hotel to obtain or return the culture plate to the housing or the hotel.

The automated system of the present invention includes a manipulator arm for moving the culture plate between the housing and the platform and placing the culture plate on the platform. The manipulator arm must have the manoeuvrability to enable it to move the culture plate from the incubator or the housing and hence it will have all of the necessary design features that enable the carrying of the culture plate to the platform.

The manipulator arm may be a robotic arm that includes a holder that is able to hold onto a culture plate when moving the culture plate from the housing. Additionally, the holder can carry the culture plate from the incubator to the platform and then to the hotel. In one embodiment the holding means is capable of grasping a culture plate. The manipulator arm must have manoeuvrability to move the culture plate from one place to another. Hence the manipulator arm is moveable in all directions including left and right, up and down and front and back and can be programmed to ensure access to the culture plates. In addition, the manipulator arm may be capable to turn its holders in order to enable turning microplates or carriers for disposable tips from portrait position to landscape position and vice versa as it may be required by the orientation of platforms, carriers, hotels or transfer stations. There may be multiple manipulator arms that not only move the culture plates but can also be programmed to fetch disposable tip carriers. The arms may be movable independently or collectively depending on the item that must be moved.

The platform is moveable preferably by tilting, shaking, rotating or any combination thereof. The shaking and rotating movements may be attained by the use of a plate vortex shaker as the platform or an orbital shaker attached to the platform. The role of the platform is to enable suitable movement to ensure that the solutions that are delivered to the culture plates are sufficiently moved around in the culture wells so as to spread the solution over the cells and to tilt the plate so that the solutions pool to enable aspiration of the solutions from the culture plate. This is important for cell detachment when using cell releasing solutions that assist in the detachment of the cells and to ensure the cells are suitably washed if the medium requires changing and to pool for collection of the detached cells.

In one embodiment the platform is programmed to tilt at a predetermined angle for a predetermined number of times sufficient to spread the medium over the cells in culture. The degree of tilting may depend on the size of the cell culture wells or the manoeuvrability of the platform. Large wells may require a greater angle of tilt compared to a smaller culture well. However, the tilt must be low or high enough to move the medium around the culture well. The number of times may also vary but the movement must be such that the medium moves sufficiently to spread the medium over the cells but not to damage the cells. In a preferred embodiment the platform is programmed to tilt for approximately 4 times at ±40° at each addition of medium. This has been found by the applicants to be sufficient to wash the cells such as for a 6 well plate.

The tilt may also enable the medium to be aspirated from the culture plate when this is necessary. The amount of tilting specified should be suitable for standard medium volumes for any given well size for spreading out the medium. However if lower volumes were used (e.g. trypsin, matrix coating) then the angle and amount of times will vary. For larger than standard volumes, tilting may not be necessary. Tilting may be required when there is insufficient solution to be aspirated so that the solution pools to substantially remove the liquid that is introduced to the culture well in the first place.

Aspiration may be performed on a tilted or non-tilted plate. However, the amount of medium or solution that is to be aspirated should ensure that sufficient solution remains so that the cells do not dry. Hence when aspirating, a predetermined volume less than the volume present in the culture well will be removed. This ensures some solution remains to prevent the culture drying.

Medium and other solutions such as PBS or culture plate coating solutions are contained in a receptacle which contains a solution to be dispensed to the culture plate. This may be a trough containing medium or a solution. However, applicants have found that the use of sterile individual receptacles or containers are better for ensuring sterility and volume of reagents required. Separate and individual receptacles reduce the risk of cross contamination for the delivery of solutions such as medium to the culture plates or wells. In other automated systems, media and solutions such as PBS are contained and delivered in tubing and troughs that are necessary for their systems. However, by preferably using separate receptacles along with the liquid handling system and a separate disposable tip assigned to an individual receptacle and a culture well, applicants have managed in one embodiment to substantially reduce any problems of cross contamination in the automated system of the present invention.

The solution will be dispensed in accordance with a programmed liquid handling system. The solutions may be dispensed singly or alternatively if any solutions are different. The automated system dispenses any solutions to the culture plates that are desirable for the maintenance and culture of cells. Solutions such as but not limited to medium, cell releasing solutions and solutions containing differentiation factors may be dispensed to the culture plates in the automated system. Solutions may also include cells in cell suspensions such as in the passaging of cells after treatment with cell releasing solutions. The cells will dislodge and the liquid handling system will pipette and dispense aliquots of cell suspension solution to a new cell culture plate.

The system also includes a disposable tip carrier for providing separate disposable tips for dispensing the solution from the receptacle to the culture plate. The disposable tip carrier contains disposable tips accessible by the liquid handling system to receive at least one tip at a time. Preferably, multiple tips are received by the liquid handling system at any time.

In another embodiment, several disposable tip carriers may be stored in a carousel. A disposable tip carrier may then be transferred from the carousel and provide disposable tips to be received by the liquid handling system. Multiple tips may be received at any one time for multiple dispensing of solution to the culture plates.

A disposable tip carrier may be any structure that can carry and hold disposable tips to be received or fetched by the liquid handling system. Preferably, the carrier would fit inside a carousel. The disposable tip carrier may be a box in which disposable tips may be suspended or a rotor that fits inside a carousel upon which the disposable tips are suspended or contained. However, the disposable tip carrier will ideally fit inside the carousel and be dispensed from the carousel to provide a continuous supply of disposable tips to the liquid handling system.

The carrier must be accessible to the liquid handling system such that the tips can be fetched. Preferably, the tips can be accessed from above. However, any point of access can be provided as long as the tip can be received by the liquid handling system and attached so that the solutions can be accurately dispensed and removed to and from the culture plate.

Multiple disposable tip carriers may be housed in the carousel for future use. They may be moved to a position that is accessible to the liquid handling system. They may be moved by the manipulator arm.

The carousel is ideally sterile. However, providing the disposable tip carriers are sterile and contain sterile tips which are presented as sterile to the liquid handling system, then it is possible that the carousel is not sterile.

In some applications a 5 mL disposable tip may be suitable, especially for delivery of medium. However, for other applications such as for cell splits, a 1 mL tip may be sufficient for delivery of the cell releasing solution or a differentiation factor. However, any sized tip may be used which fits a corresponding carrier and which may be received by the liquid handling system.

Depending on the tip used, the liquid handling system can be programmed such that the solutions are controllably delivered without dispersion. The vacuums and pressures required for dispensing from a 5 ml disposable tip would be different to those required for a 1 ml tip.

Also the tips may be selected based on the size of the culture wells.

The tips are sterile and disposable and preferably contain a filter. Disposable filtered tips are preferred, as fixed tips can easily carry contaminations and the sterility of the automatic system is paramount. There is also the risk of cross-contamination of samples by using fixed tips, thus the use of sterile disposable tips, preferably filter tips for all liquid handling procedures may be incorporated into the automated system.

Preferably, the use of disposable tips allows for a separate disposable tip to be assigned to a receptacle and a culture well. This is advantageous to ensure cross contamination is not carried over to other wells if medium is to be delivered to the wells. This is also paramount for the passaging of cells. It is imperative that all possibilities of cross contamination are alleviated in the automated system such as in the process of passaging and cell spitting. The use of the disposable tip carrier and separate disposable tips allows for the separate processing of each culture well without the concerns of cross contamination.

Multiple disposable tips may be received by the liquid handling system for dispensing a solution to multiple culture wells. Separate tips are desirably used when using different solutions such as media, cell releasing solutions, differentiation factor or PBS. A separate tip may be used each time a separate solution is to be dispensed.

Bringing the delivery of medium to the culture plate is a liquid handling system for interacting with the disposable tip carrier and the disposable tips and the individual receptacles to deliver to and remove solution from the culture plates. The liquid handling system may include an arm to fetch and discard disposable tips that is manoeuvrable between the disposable tip carrier, the receptacle and the culture plate which enables a predetermined amount of solution to be aliquoted in the separate disposable tip for delivery to or from the culture plate.

The arm may be a robotic arm that includes at least one pipetting channel to pipette and dispense solutions to and from the culture plate. Manoeuvrability is necessary to transfer solutions between the receptacle and the culture plate and hence the arm should be moveable in all directions including left and right, up and down and front and back and can be programmed to ensure access to the disposable tip carrier and the receptacle for dispensing solutions. The liquid handling system may comprise multiple arms allocated to the different roles such as dispensing and removal of solutions from the culture plate. However, a single arm may also be adapted for the role. The arms may be movable independently or collectively.

The liquid handling system may have a means to apply a vacuum or pressure to dispense or remove solution from the cell culture plates and the vacuum or pressure can be connected to the disposable tip for dispensing and removal of solution.

The liquid handling system can be programmed to remove a volume of solution less than a volume of solution present in the culture well prior to delivering a volume of solution or medium to the culture well suitable to maintain the reprogrammed somatic cells. The purpose of this is to ensure that solution is left in the culture well ensuring that the cells do not dry out. In some cases, as little as 100 µL may be left in the well to ensure the cells do not dry out.

Additionally, the liquid handling system may be programmed to remove and dispense predetermined amounts of cell releasing solution or differentiation factor. Hence the liquid handling system may have multiple delivery modes that allow one system to be responsible for delivering all solutions at appropriate times. To remove and dispense these solutions, the liquid handling system is also programmable to interact with a disposable tip carrier carrying tips suitable for the solution and to fetch the disposable tips, cell releasing solution or differentiation factor that must be dispensed and to select the appropriate tip for the solution.

The liquid handling system will have incorporated a vacuum or pressure system which enables aspiration of a defined aliquot of liquid to be received by the disposable tips. Similarly, the liquid handling system must be able to dispense of an aliquot of liquid to the cell culture plates. Hence a vacuum or pressure system is suitable for delivery to and removal of solution to and from the culture plates.

Such a system of vacuum and pressure will assist in controllably dispensing or removing solution from the culture plates.

The vacuum system may be provided by a pump system such as a liquid or air displacement pump. Applicants have found that a liquid filled pump is effective. However, the pump must be carefully controlled so that when dispensing media to the culture wells, the medium is not delivered too quickly so that the medium is dispersed outside the culture and increases cross contamination between cultures. Conversely, the pump must be carefully controlled to remove predetermined aliquots of medium.

Hence, applicants have found that in the automated system, it is imperative that the solutions are controllably delivered to and removed to reduce the risk of contamination.

When using a liquid filled liquid handling system, applicants have found that liquid from the pump can foul the tubing and cause contamination. Additionally, when removing medium, the pump must be controlled so that an air pocket is not introduced into the disposable tip to cause inaccurate removal of aliquots of medium. In addition, the movement of the pipetting channel in a z-direction must be controlled either by automated liquid level sensing of the medium and subsequent submerging into the medium or by moving down the pipetting channel just to the bottom of the well for preventing air aspiration. Hence it is imperative that the solutions are controllably and sterilely dispersed and removed to enable consistent reproducibility, and automatic cell culturing.

A suitable liquid filled liquid handling system may comprise a syringe pump for precisely adjusting vacuum and pressure. Tubing will connect the syringe pump to an adapter which may be further moved by the manipulator arm or by a separate robotic arm (liquid handling arm) to fetch and dispose the disposable tips. The syringe pump may be connected to a system liquid container by a system liquid tubing. The incompressible liquid in the tubing, along with the syringe pump can be controlled to provide vacuum and pressure to the disposable tip. The syringe pump may further comprise a multi valve such as a three way valve for switching pumping action between the system liquid container and the disposable tip. The system liquid container, the system liquid tubing, syringe of the syringe pump and the multi valve and tubing may be filled with system liquid, preferably with sterile deionised water.

Another liquid handling system for providing the necessary vacuum and pressure for dispensing and removing solution may be provided by an air displacement liquid handling system. The air displacement liquid handling system may comprise a piston which travels within an airtight sleeve. Vacuum and pressure is created in the space left vacant or displaced by the piston. The space is fluidly connected to the fetched disposable tip.

A controlling system is provided to automate and program any one of the manipulator arm, the platform and the liquid handling system such that the liquid handling system controllably and sterilely delivers and removes individual aliquots of medium to and from the culture plate before the manipulator arm optionally returns the culture plate to the housing. The controlling system may be a computer system adapted to integrate with the manipulator arm, the platform and the liquid handling system to control manoeuvrability of the manipulator arm, movement of the platform and delivery of predetermined volumes of solution from the liquid handling system.

All of the manipulator arm, the platform or the liquid handling system may be automated or programmed using the controlling system or at least one is automated or programmed to automate some aspect of the automated system. Ideally, all are automated or programmed together.

The cells may be washed using the automated system of the invention with any solution that is not detrimental to the cells such as cell culture medium or phosphate buffered solution (PBS). This may be used prior to the introduction of other factors, such as but not limited to differentiation factors. However, the automated system is particularly useful for maintaining the cells by changing medium in cell culture plates.

The automated system as herein described may also be used to coat culture plates with factors such as matrices and peptides that support cell growth, preferably stem cell growth. For instance, factors such as vitronectin, laminin or matrigel, or even human or mouse feeder layers may be coated on the culture plates using the automated system of the present invention. However, these methods will be known and available to the skilled addressee.

The automated system may also incorporate pre-coated plates or plates with modified surfaces that support stem cell growth and/or differentiation. The plates may be adapted to fit the automated system by integrating with any of the platform, the manipulator arm or the liquid handling system so that the manipulator arm can move or dispense of the culture plate, the platform can receive and move the cell culture plate and the liquid handling system can deliver and remove individual aliquots of medium to and from the culture plate before the manipulator arm optionally returns the culture plate to the housing.

The automated system of the present invention is advantageously adaptable as a modular system integrating other components such as an incubator and a hotel for storage and incubation of culture plates during processing of culture plates through the automated system. These additional modules may complement the automated system to enable greater efficiencies during the processing steps. In another embodiment the automated system further includes a waste container for used disposable tips or a cell sorting unit for sorting differentiated cells from non-differentiated cells.

Additionally, the automated system may be housed in a biosafety cabinet to improve sterility during the processing of culture plates. In one embodiment any one or the entire platform, individual receptacles for containing medium and disposable tip carrier are housed in a biosafety cabinet. In another embodiment, the biosafety cabinet further includes the liquid handling system and the manipulator arm. Preferably, the biosafety cabinet is a class 2 biosafety cabinet.

In yet another aspect of the invention there is provided an automated system for sterile passaging of cells, said system comprising:
  a platform for receiving and moving a cell culture plate from a housing;
  a manipulator arm for moving the culture plate between the housing and the platform and placing the culture plate on the platform;
  a receptacle for containing a sterile solution or a cell releasing solution to be dispensed sterilely to the culture plate;
  a disposable tip carrier for providing sterile disposable tips for dispensing the solution or a cell releasing solution from the receptacle to the culture plate;
  a liquid handling system which interacts with the disposable tip carrier, and the receptacle to controllably and sterilely dispense to and remove solution and the cell releasing solution from the culture plate such that the solution or the cell releasing solution is sterilely dispensed without dispersion outside the stem cell culture and removed at a predetermined volume; and
  a controlling system to automate and program any one of the manipulator arm, the platform, and the liquid handling system such that the liquid handling system controllably and sterilely delivers and removes predetermined aliquots of solution and cell releasing solution to and from the culture plate sufficient to detach the cells from the culture plate for further passaging.

The automated system of the present invention may be used to maintain cell lines by ensuring passage of the confluent cultures. Cell cultures may be removed automatically from the incubator and the cells detached from the cultures and seeded to a new culture plate all via the automated system of the present invention.

This may be achieved by incorporating an additional dispenser or be incorporated into the liquid handling system to dispense a cell releasing solution from a reservoir such as but not limited to ethylenediaminetetraacetic acid (EDTA), trypsin, ReLeSR™ Trypsin-EDTA, TrypLE™ Express, TrypLE™ Select, Collagenase, Dispase, Phosphate Buffered Saline, Accutase™, Accumax™, Cell dissociation solution (Sigma-Aldrich), Cell dissociation buffer (Thermofisher). However, any solutions known and available to the skilled addressee would be suitable to release the cells from the culture plates.

The dispenser may be a separate dispenser, or may be part of the laboratory automation platform or the liquid handling system that delivers medium to the cell culture plate used for the delivery of the cell releasing solution instead of medium. In this situation, the liquid handling system accesses a separate source or receptacle containing the cell releasing solution and aliquots a predetermined amount of solution to or from the culture plate.

Cross contamination of solutions is avoided by the use of separate disposable tips from the disposable tip carrier and the preferable use of individual receptacles to deliver to and remove medium and the cell releasing solution from the culture plate where a separate disposable tip is assigned to an individual receptacle and culture well for delivery and removal of the media. At least one disposable tip carrier can be used for providing sterile disposable tips for dispensing solution or cell releasing solutions, or separate disposable tip carriers can be incorporated into the automated system. If this is the case, the liquid handling system can be programmed to access tips from either carrier depending on the solution to be delivered.

The automated system can be programmed to reuse disposable tips as the same tip can be used for the same culture well, providing it is used in a non-contaminating manner. For instance, if (1) medium is delivered to the well and (2) subsequently immediately removed following a washing step, the same disposable tip can be used and programmed into the automated system for the two steps. Generally, the disposable tips are not reused so as to avoid cross contamination and to maintain sterility.

Any cell releasing solution may be used to detach the cells from the culture plate. However, the liquid handling system may be programmed so that the cell releasing solution is incubated with the cells for a time that is sufficient to detach the cells. This may be dependent of the cell releasing solution used and the mode of action. This may be optimized by the skilled addressee familiar with the characteristics of the cell releasing solution or method.

The cell culture plates will be placed on the platform by the manipulator arm and the platform is programmed to move at a predetermined angle for a predetermined number of times sufficient to spread the cell releasing solution over the cell culture. Depending on the size of the culture plate and the volume of cell releasing solution used, the predetermined angle for a predetermined number of times sufficient to spread the cell releasing solution over the cell culture can be determined.

Preferably the platform is programmed to tilt for approximately 20 times at ±10° to rinse the cells.

Preferably the platform is programmed to tilt for approximately 20 times at ±10° with the cell releasing solution exposed to the cells.

Preferably the platform is programmed to tilt for approximately 4 times at ±40° to change medium.

Preferably the platform is programmed to shake and tilt for approximately 100 times±5°; approximately 20 times±40°, and then approximately 1000 times±0.5° to detach the cells.

Preferably the platform is tilted at an angle sufficient to pool the medium and cells for aspiration. Ideally the tilt must be high or low enough so as to reduce the risk that cells will be left behind on the culture surface. The tilt may be as high as the maximum tilt of the platform which for some machines is approximately 52° angle to aspirate and collect the cells following detachment from the culture plate for further passaging.

Once the cells are released from the culture plate and aspirated, a split ratio for each culture plate for passaging cells is determined from a user defined optimum density.

Preferably, the split ratio is in the range of 1:1 to 1:6, preferably 1:1 to 1:5, or 1:1 to 1:4, or 1:1 to 1:3 or 1:1 to 1:2 because of the use of 5 mL tips. However, a ratio from 1:1 to 1:384 is feasible but would require smaller tips or greater volumes of medium. This range may vary depending on the medium used. For instance, the range may be higher if it is optimised.

In another aspect of the present invention, there is provided an automated system for sterile differentiation of cells, said system comprising
- a platform for receiving and moving a cell culture plate from a housing;
- a manipulator arm for moving the culture plate between the housing and the platform and placing the culture plate on the platform;
- a receptacle for containing a sterile solution or a differentiation factor to be dispensed controllably and sterilely to the culture plate;
- a disposable tip carrier for providing sterile disposable tips for dispensing the solution or differentiation factor from the receptacle to the culture plate;
- a liquid handling system which interacts with the disposable tip carrier and the receptacle to controllably and sterilely deliver to and remove solution or differentiation factor from the culture plate such that the solution or the differentiation factor is sterilely dispensed without dispersion outside the stem cell culture and removed at a predetermined volume; and
- a controlling system to automate and program any one of the manipulator arm, the platform, and the liquid handling system such that the liquid handling system controllably and sterilely delivers and optionally removes predetermined aliquots of solution or differentiation factor to and from the culture plate and optionally the manipulator arm returns the culture plate to the housing.

Once the cells are suitably cultured they may undergo differentiation if they are of the cell type capable of doing so. For instance, if the cells that are cultured are PSCs or iPSCs, they will be capable of differentiation to a somatic cell type by the introduction of a differentiation factor determined for the desired somatic cell type.

The differentiation factor may be delivered to the cells by a separate differentiation unit capable of dispensing a differentiation factor or factors. Similar to the dispenser for dispensing a cell releasing solution, the differentiation unit may be a separate unit, or it may be the same liquid handling system that delivers medium to the cell culture plate but is programmed to incorporate another action that allows the delivery of the differentiation factor or factors instead of medium. In this situation, the liquid handling system accesses a separate receptacle containing the differentiation factor or factors and aliquots a predetermined amount of differentiation factor or factors to the culture plate.

Various differentiation factors are available to the skilled addressee familiar with stem cell technology. Preferably the differentiation factor is a single factor or is a mixture of factors inducing differentiation together. In this case, the differentiation factors may be premixed or added separately from individual receptacles and delivered by suitably programming the liquid handling system to interact with the disposable tip carrier and the individual receptacles containing differentiation factor or factors.

In a preferred embodiment the automated system further includes a cell sorting unit for identifying differentiated cells. This may be integrated into the automated system or may be provided as a modular unit alongside the automated system. Additionally, this may be conducted offline to the automated system.

In order to assess pluripotency such as for quality control, TRA-1-60 quantifications can be performed using a MACSQuant (Miltenyi) on iPSCs just prior to passaging to fresh plates, and at different passage numbers. Cell counts of live cells when plated down and at passaging can be performed to determine cell growth.

Other cell surface markers specific to pluripotent stem cells may also be used including but not limited to, GCTM2, Tra-1-81, SSEA3 and SSEA4. Cell enrichment and purification steps could also be performed by Fluorescence-activated cell sorting using 1 or more antibodies, with or without dyes to determine cell viability.

Cells can also be enriched by TRA-1-60 selection using MACSQuant. However, any enrichment method may be used to separate different cell types depending on the cell types that have been cultured in the automated system.

Persons skilled in the art can utilize any cell sorting or identification processes before plating or passaging by using the automated system of the present invention.

Other aspects of the present invention will become apparent to those ordinarily skilled in the art upon review of the following description of specific embodiments of the invention.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

The present invention will now be more fully described by reference to the following non-limiting Examples.

EXAMPLES

The following examples describe a customized Freedom EVO laboratory automation platform for the maintenance of human fibroblasts undergoing reprogramming to iPSCs, as well as maintenance and passaging of undifferentiated colonies of PSCs. The feasibility of using this laboratory automation platform for long term differentiation of cells is described, demonstrated with guided differentiation of human PSCs to retinal cells, including retinal ganglion cells (RGCs) and retinal pigment epithelium (RPE) cells. The maintenance protocols employed and the adaptations required for using this laboratory automation platform are described. This system allows for large sample sized research, reduced variability and allows for future high-throughput analysis of the transcriptome and metabolome of progeny cells derived from patient iPSCs. The system enables the maintenance of human fibroblasts undergoing reprogramming, the long-term maintenance, passaging and differentiation of iPSCs, which are not available with smaller liquid handlers, and offers an economical alternative to more complete equipment. However, it will be appreciated that the system can be adapted for other somatic cell types including fibroblasts for generating the iPSCs.

Materials and Methods

Ethics.

All experimental work performed in this study was approved by the Human Research Ethics committees of the Royal Victorian Eye and Ear Hospital (11/1031H, 13/1151H-004) and University of Melbourne (0605017, 0829937) with the requirements of the National Health & Medical Research Council of Australia (NHMRC) and conformed with the Declarations of Helsinki[12].

Platform Material.

The Tecan system is a liquid handling and robotic laboratory automation platform that requires a tissue culture plate format. All cells were cultured and handled in a 6-well plate format. Tips used were 5 mL disposable conductive sterile tips with filter which can be fetched by and discarded from Liquid Handling arm. Cell culture medium was aliquoted into 50 mL falcon tubes and placed into specific carriers in the Tecan laboratory automation platform.

Fibroblast Culture.

Human fibroblasts were cultured in DMEM with high glucose, 10% fetal bovine serum (FBS), L-glutamine, 100 U/mL Penicillin and 100 µg/mL streptomycin (all from Life Technologies). All cell lines were confirmed to be *mycoplasma*-free using the MycoAlert *mycoplasma* detection kit (Lonza) per the manufacturer's instructions. A total of 77 fibroblast lines were used for reprogramming.

Generation of iPSCs.

iPSCs were generated using human skin fibroblasts obtained from subjects over the age of 18 years by episomal method as described previously[13]. Briefly, reprogramming was performed on passage 8-10 fibroblasts by nucleofection (Lonza Amaxa Nucleofector) with episomal vectors expressing OCT4, SOX2, KLF4, L-MYC, LIN28 and shRNA against p53 14 in feeder- and serum-free conditions using TeSR-E7 medium (Stem Cell Technologies). The reprogrammed cells were maintained on the automated platform using TeSR-E7 medium, with medium change every day (2 mL/well).

Selection of iPSCs.

Pluripotent cells were selected using a MultiMACS (Miltenyi) by TRA-1-60 sorting using anti-human TRA-1-60 Microbeads in combination with MultiMACS Cell24 Columns (Miltenyi). Briefly, reprogrammed cells from 1 well of a 6-well multiwell plate were washed in PBS, incubated with TrypLE (5-10 mins, 37° C.) and cells were collected and gently triturated in TeSR-E8 medium supplemented with Y27632 (10 µM). The cell suspension was filtered through a pre-separation filter (30 µm, Miltenyi) into a 15 mL tube, cell number was determined. Cells were then centrifuged (5 min, 300 g) and resuspended in 80 µL ice-cold TeSR-E8 medium containing Y27632 (10 µM), and incubated with 20 µL anti-TRA-1-60 beads (5 mins, 4° C.). Volume was adjusted to 1 mL in TeSR-E8 medium containing Y27632 (10 µM) and each suspension containing magnetically labelled cells was loaded onto a MultiMACS column. Columns were washed twice with TeSR-E8 medium containing Y27632, then eluted with 1 mL TeSR-E8 medium containing Y27632. Cell number was determined and cells were then plated into 1 well of a 6-well plate coated with vitronectin XF (40 µL/well in 2 mL cell adhere dilution buffer Stem Cell Technologies), then placed back into the online incubator. Quantification of successful reprogramming was performed post-TRA-1-60 selection by immunomagnetic beads (MACS), measuring frequency of lines able to form undifferentiated colonies, no colony or colonies of differentiated cells. Frequency of reprogrammed fibroblasts that formed small colonies that did not grow was also reported.

Maintenance and Passaging of PSCs.

Subsequent culturing was performed on the automated platform using TeSR-E8 (Stem Cell Technologies), changing medium every two days (2 mL/well). Passaging of 10 newly generated iPSC lines and of the iPSC line CERA007[15] was performed on the automated platform using ReLeSR™ (Stem Cell Technologies) onto vitronectin XF plated wells. In parallel, iPSCs and the human embryonic stem cell line H9 (Wicell) were maintained in the same conditions but manually passaged as a comparison to automation.

Automated Passaging.

Passaging was performed weekly.

(a) Preparation of Vitronectin XF Coated Plates

New vitronectin coated plates were accessed from the incubator, placed on the platform 4 at a time. Vitronectin XF was removed, approximately 2 mL of PBS was added per well, the platform was tilted approximately 4 times to ±40°, PBS was removed, approximately 2 mL of medium was added then the platform was tilted approximately 4 times to ±40° and plates were returned to the incubator or a hotel to house or park the plates until they are required to receive cells.

(b) Passaging of Cells

In parallel, the plates to be passaged were retrieved from the incubator and placed onto platform (4 at a time), medium was removed, approximately 1 mL of PBS was added and the plate carrier was tilted approximately 20 times to ±10°. PBS was removed, replaced by 800 µL of ReLeSR™ and the plate carrier was tilted approximately 20 times to ±10° or until the ReLeSR™ was sufficiently spread over the cells. The plate carrier was tilted as follows for change of liquid: approximately 4 times to ±40° for washes with PBS; approximately 20 times to ±10° when shaking was needed. 700 µL of ReLeSR™ was removed and cells were left to incubate for 10 min. Medium (approximately 1 mL) was added for 3 min, followed by shakes of the carrier (for instance tilt 100 times±5°; 20 times±40°, 1000 times±0.5°) twice. It was found that this combination of tilt times and angle was optimal for detaching cells. However, slight variations of the combination may also suffice to detach the cells. Visual assessment of cell detachment was then performed. Medium was then aspirated with an approximately 52° angled carrier, and transfer to 15 mL tubes (6 wells into 1 tube: final volume of 4.8 mL). Cell suspension was mixed by pipetting up and down 2 times with 4 mL medium and seeded into the Vitronectin XF-coated plates of (a) above that were retrieved from the hotel at a chosen concentration, and returned to the incubator.

Quantification of Expression of Pluripotency Markers and of Cell Growth.

TRA-1-60 quantifications were performed using a MACSQuant (Miltenyi) on iPSCs just prior to passaging to fresh plates, and at different passage numbers. Cell counts of live cells when plated down and at passaging were performed to determine cell growth.

Retinal Cell Differentiation.

Retinal differentiation of BRN3B-mCherry A81-H7 hESCs 16 was performed via an adapted protocol originally described by Lamba, D. A.; Karl, M. O.; Ware, C. B., et al., (2006)[17] using DMEM F12 with glutaMAX (Life Technologies), 10% Knockout Serum Replacement (Life Technologies), IGF1 (10 ng/mL, Peprotech), Dkk1 (10 ng/mL, Peprotech), Noggin (10 ng/mL, R&D Systems), bFGF (5 ng/mL), B27 and N2 (both 1×, Life Technologies) as described in Gill, K. P.; Hung, S. S.; Sharov, A., et al (2013)[18], changing medium every second day. The protocol was adapted to automation by starting with a monolayer of PSCs plated on vitronectin XF in place of embryoid body formation. Cells were assessed at day 24 and no further enrichment was performed Gill, K. P.; Hung, S. S.; Sharov, A., et al (2013)[18]. Successful differentiation into RGCs was determined by appearance of mCherry positive cells, which is indicative of BRN3B expression. Differentiation of H9 hESCs (Wicell, USA) into RPE cells was performed in feeder-free conditions as described in Lidgerwood, G. E.; Lim, S. Y.; Crombie, D. E., et al.[19] using vitronectin XF and RPEM medium (α-MEM, 0.1 mM Non Essential Amino Acids, 0.1 mM N2, 1% L-Glutamine-Penicillin-Streptomycin solution, 250 μg/mL Taurine, 20 ng/mL Hydrocortisone, 13 μg/mL Triiodothyronine (all from Sigma-Aldrich), 25 mM HEPES), supplemented with 5% FBS, IGF1 (10 ng/mL), Dkk1 (10 ng/mL), Noggin (10 ng/mL), bFGF (5 ng/mL), B27 and N2 (both 1×), changing medium every two days. Cells were assessed at day 35. Successful differentiation into RPE cells was determined by cobblestone morphology and pigmentation, as well as PMEL expression by immunocytochemistry.

Immunocytochemistry.

Immunocytochemistry was performed using OCT3/4 (C-10, Santa Cruz), TRA-1-60 (Abcam) and PMEL (Abcam). Cells were then immunostained with isotype-specific secondary antibodies (Alexa-Fluor, Life Technologies). Nuclei were counterstained using DAPI (Sigma-Aldrich).

Statistical Analysis.

Data are expressed as mean±standard error of the mean (SEM). All statistical analyses and graphical data were generated using Graphpad Prism software (v6, www.graphpad.com). TRA-1-60 quantifications were performed on 10 individual lines maintained on the automated laboratory automation platform (n=5 at passage 1 and n=5 at passage 4), as well as 3 lines maintained manually. Cell counts were performed on 11 individual iPSCs lines over 3 passages each. Statistical methods utilised were One-way ANOVA followed Tukey's multiple comparisons test. Statistical significance was established from p<0.05.

Example 1: Description of the Laboratory Automation Platform

Figure 1B:
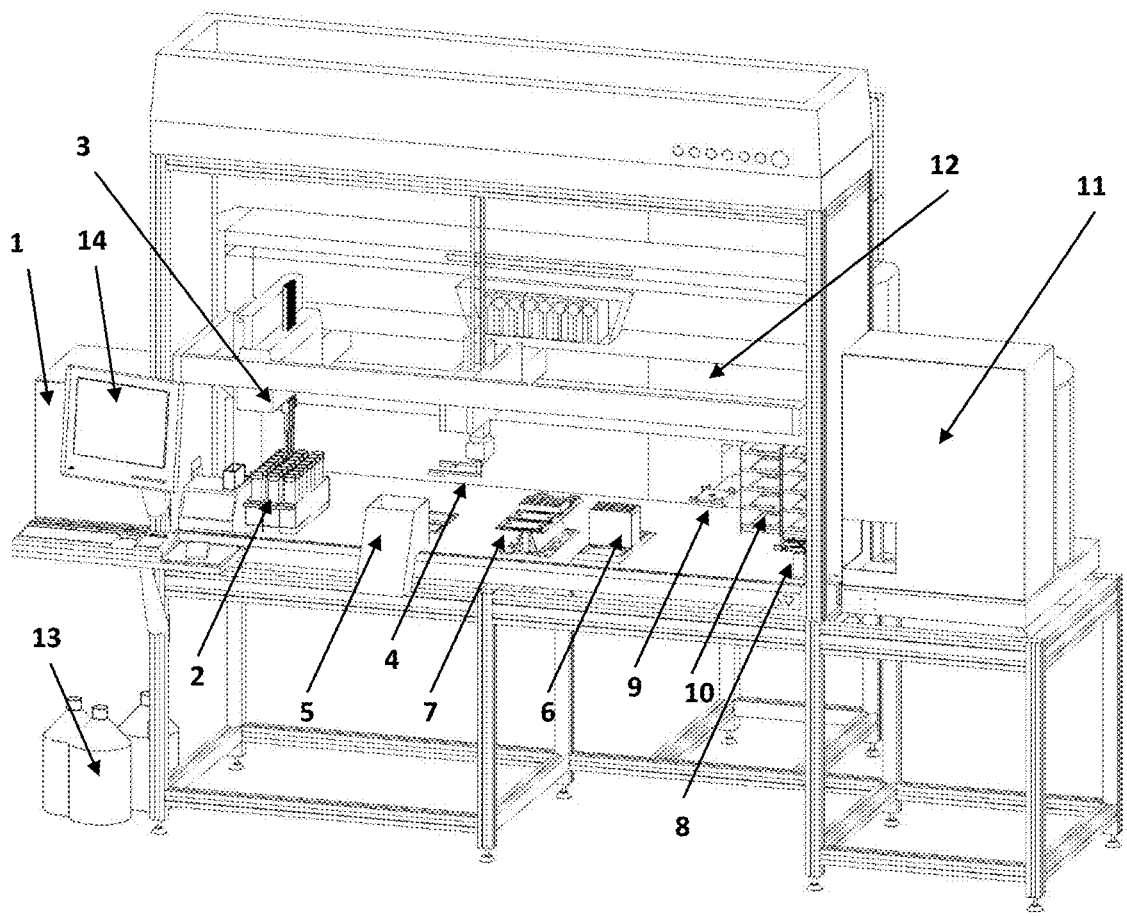
FIG. 1B shows CAD images of an angled view of the laboratory automation platform.
Figure 1C:
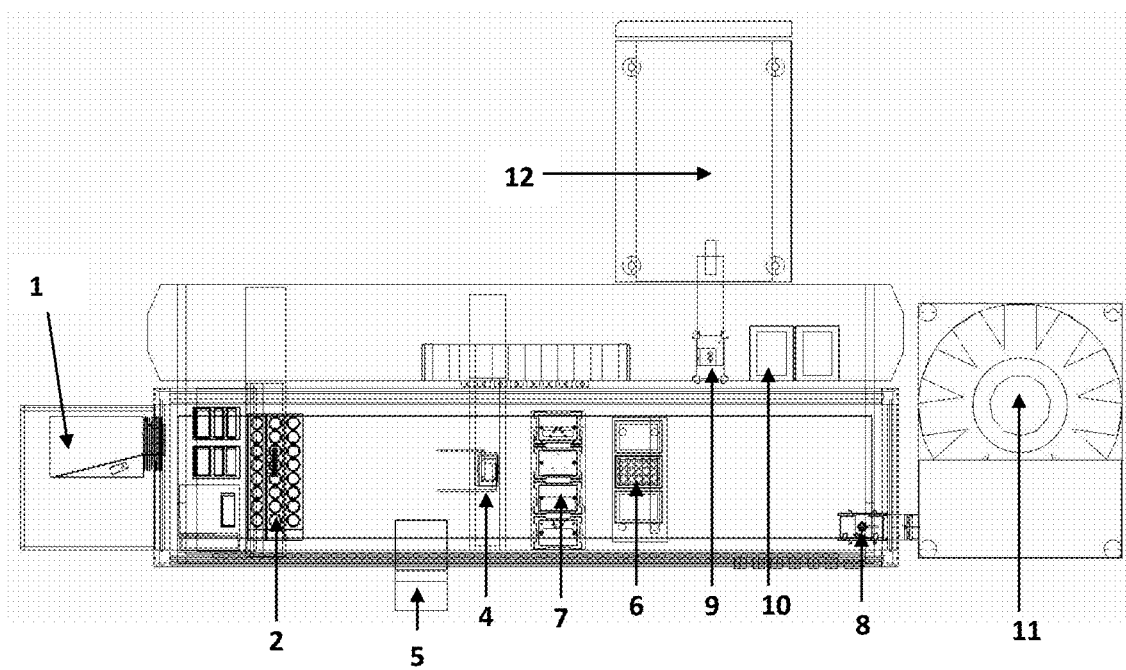
FIG. 1C shows (CAD) images of the laboratory automation platform from top.

The modular laboratory automation platform is comprised of a Freedom EVO® 200 instrument—that includes a class 2 biosafety cabinet, a robotic liquid handling arm with 8 independent channels and a robotic manipulator arm—in conjunction with a Liconic STX110 automated incubator mounted behind the Freedom EVO®, and a carousel LPX220 for disposal tip carriers on the right side of the working platform (FIG. 1). A 5 L glass bottle and peristaltic pumps are also present; however, these were not used for the routine maintenance described here.

Tubing and troughs necessary for the bottle and peristaltic pumps were not used but were replaced with sterile Falcon tubes as a means to ensure sterility and volume of reagents required (FIG. 1). The overall system dimensions are 3.4 m (L)×1.8 m (W)×2.7 m (H). To the left side, some space was reserved for a computer, keyboard, monitor and operator (FIG. 1). A MultiMACS24 Separator and a MACSquant flow cytometer were accessed offline.

As illustrated in FIG. 1, on the workbench, from left to right, are a cabinet with medium bottle and pump (1) which can deliver medium to a medium refill trough contained within a Torrey Pines heater; 3 carriers for up to 24×50 mL Falcon tubes (2), robotic liquid handling arm (3), manipulator arm (4), a large waste for disposable tip carriers and used tips (5), a carrier for disposable tips (6), a tilting platform (7), transfer station for carriers for 5 mL disposable tips (8), the transfer station (9) to the Liconic incubator (12), a hotel for tissue culture lids (10) and a carousel (11), a computer (14). Autoclaved water bottles for the liquid handling system were stored under the bench (13). The liquid handling system was equipped with 5 mL syringes: 8×5 mL syringes for large disposable tips use, though are capable of handling smaller 1 mL tips (which were not used for this protocol). The Liconic LPX220 carousel was used for the storage of tip boxes. It contains 1 rotary plate with 10 interchangeable cassettes and an internal robotic handler, as well as a transfer station to place tip boxes onto the worktable. The Liconic STX110 incubator comprises of an internal robotic handler to access 5 independent stackers that can store up to 85 culture plates (17 per stacker), an internal barcode scanner as well as a transfer station to bring culture plates onto the worktable. The incubator has a controlled environment, which was set to 37° C. and 5% $CO^2$. The Freedom EVO® runs with two independent software packages: the Freedom EVOware® Plus controlling software (Tecan Switzerland AG)) and the Workflow Planning Tool. These are used to direct pipetting, liquid handling arm, manipulator arm, tilting platform and also Liconic STX110 incubator and Liconic LPX220 carousel as well; and to plan and execute each line of the workstation's workflow (the Workflow Planning Tool). Each protocol used on the platform was entered as an independent template.

Example 2: Generation of iPSC Lines 77 skin fibroblast lines from individual patients to iPSCs using episomal vectors in feeder- and serum-free conditions in TeSR-E7 medium were manually reprogrammed. Nucleofection of fibroblasts was performed in a 6-well plate format. Following nucleofection, cells were placed into the online incubator. Medium was changed every day using the laboratory automation platform. To identify and isolate iPSCs, the marker TRA-1-60 was utilized which was previously shown to be a marker of fully reprogrammed iPSCs[20]. Instead of picking clonal-derived iPSCs, bulk selection of polyclonal iPSCs was performed as these were shown to be indistinguishable from clonal-derived iPSCs. Notably, the bulk generation of polyclonal iPSCs has been shown to be as effective in the generation of fully reprogrammed lines as manual selections of clones[21]. At approximately day 30, iPSCs were purified by MACS labelled with TRA-1-60, using a MultiMACS24 Separator and maintained in feeder-free culture on vitronectin in TeSR-E8 medium. When post-reprogrammed cells were subjected to TRA-1-60 selection by MACS for selection of iPSCs, 52.31±5.71% of whole cells sorted for TRA-1-60 were positive for the pluripotency marker, and were plated for expansion (Table 1). Quantification of reprogramming performed post TRA-1-60-MACS enrichment indicates that 92.2% of fibroblast cultures were successfully reprogrammed to iPSCs (presence of TRA-1-60 positive colonies which had grown and retained their characteristic undifferentiated morphology), whilst 2.6% of fibroblast cultures formed small colonies that did not grow, and 5.2% of reprogrammed fibroblast cultures formed no colony or colonies of differentiated cells (n=77, Table 1).

TABLE 1

Quantification of successful reprogramming

| | |
|---|---|
| Initial number of fibroblast lines reprogrammed (%) | 77 (100) |
| Number successfully reprogramed (%) | 71 (92.2) |
| Number of lines MACS sorted, which failed to thrive (%) | 2 (2.6) |
| Number of lines with no colonies or only differentiated colonies present after reprogramming (%) | 4 (5.2) |
| % TRA-1-60 positive cells post reprogramming (Mean ± SEM)* | 52.31 ± 5.71 |

Figure 2:
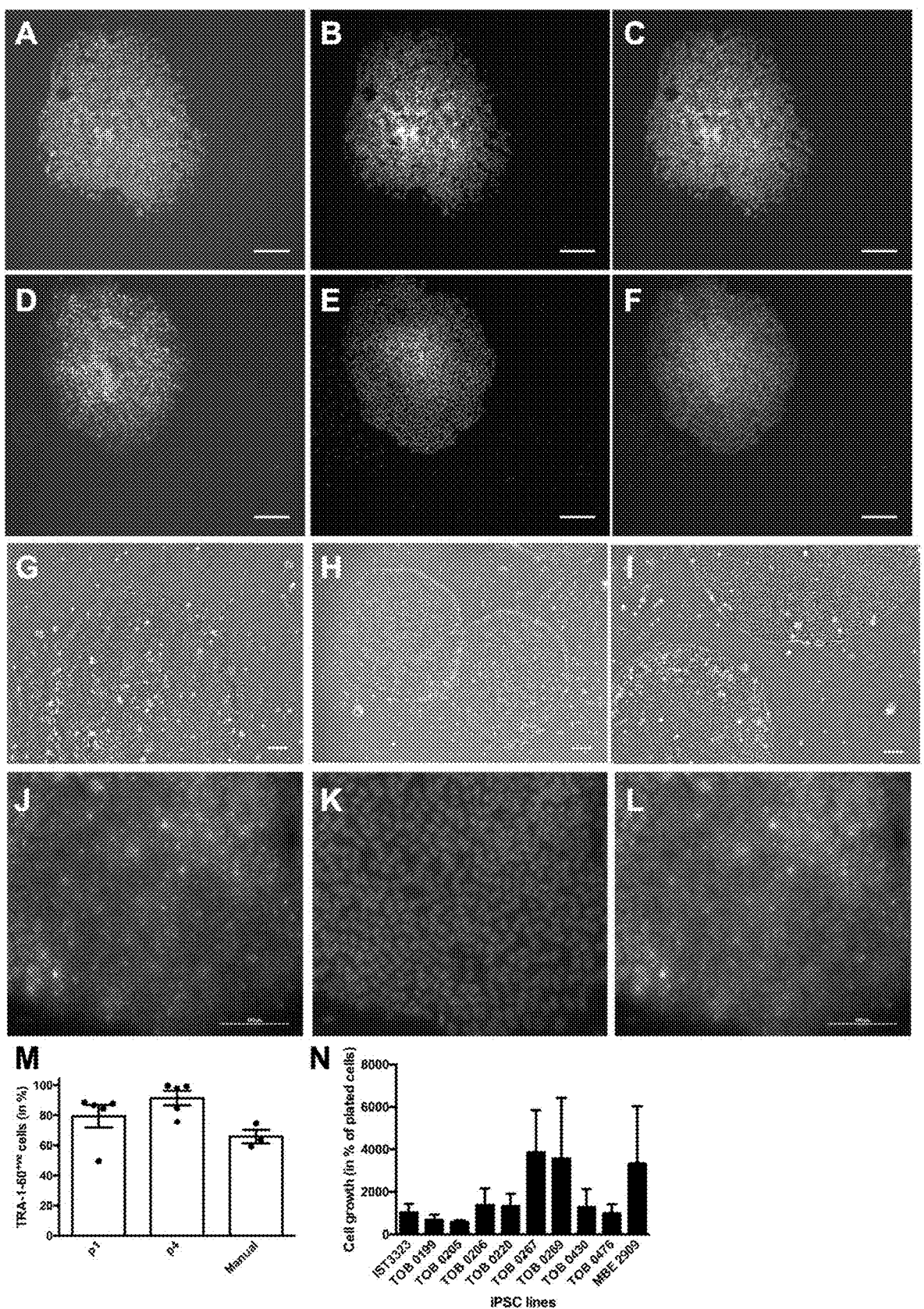
FIG. 2 shows stem cell maintenance using the automated laboratory automation platform. (A-F) Maintenance of cells post-TRA-1-60 selection. Representative images of colonies post-TRA-1-60 sorting, immunostained for OCT-4 (A) or TRA-1-60 (D) with DAPI counterstained (B, E) and merged (C, F). (G-L) Passaging. Representative bright field (G-I) and fluorescent (J-L) images of undifferentiated iPSCs after passage 1 (G), 3 (H) and 4 (I) and immunostained for OCT-4 and TRA-1-60 at passage 4 (J) with DAPI counterstained (K) and merged (L). Scale bars: A-F: 250 µm; G, I-L: 100 µm; H: 300 µm. (M) Scatter plot with bar of the TRA-1-60 positive (+ve) cells just prior to passaging, in 10 independent cell lines and at two different passages (p1: n=5, p4: n=5) maintained on the laboratory automation platform and in iPSCs and human embryonic stem cells H9 manually maintained in similar conditions (manual, n=4). Data are mean±SEM of independent lines. One-way ANOVA followed Tukey's multiple comparisons test indicate no statistical difference between conditions. (N) Growth rate of 10 individual iPSC lines over 3 passages, represented as the ratio of final cell number to cell number when plated down and presented in %. Each column represents mean±SEM of 3 successive passages of individual lines. One-way ANOVA followed by Tukey's multiple comparisons test suggest no statistical difference between conditions.

*n = 51 samples were sorted and satisfied internal specifications for cell counts and cell sizes on countess Example 3: Maintenance of PSCs iPSC lines were then used for maintenance and passaging on the laboratory automation platform. Pluripotency of all derived iPSC lines was further evidenced by immunocytochemistry for OCT-4 and TRA-1-60 expression (FIG. 2A-F). The maintenance and passaging templates allow for changing medium and passaging of iPSCs. Maintenance was optimized for automation in serum-free and feeder-free conditions using vitronectin-coated plates in TeSR-E8 medium. All lines were successfully passaged on the laboratory automation platform. iPSCs were maintained for multiple passages on vitronectin-coated plates using E8 culture medium and passaged using ReleSR. Representative bright field images of colonies following successive passaging are shown in FIG. 2G-I. Immunocytochemistry confirmed that iPSCs remain pluripotent, as indicated by OCT-4 and TRA-1-60 expression, following successive passaging using this laboratory automation platform (FIG. 2J-L). Cells were passaged at a split of 1:6 without affecting maintenance and morphology. MACS quantification of TRA-1-60 immediately prior to passaging demonstrates that the cells were successfully maintained pluripotent on the laboratory automation platform. Lower splits would be achievable using 1 mL tips in place of 5 mL tips. Indeed, as shown in FIG. 2M, the quantification of TRA-1-60, across lines and across passaging clearly indicates reproducibility and little variability in TRA-1-60 expression, with 79.45±7.51% (passage 1, n=5 lines quantified) and 91.49±4.81% (passage 4, n=5 lines quantified) of TRA-1-60 positive cells in the culture. In parallel to the automated maintenance of iPSCs, some iPSCs lines and H9 were also manually cultured, using the same feeder-free and serum-free conditions. Quantification of TRA-1-60 just prior to passaging indicate that 65.91±4.56% cells were TRA-1-60 positive (FIG. 2M, n=4 lines quantified), indicating that automation is at least equivalent to manual maintenance in generating high quality pluripotent iPSC colonies, and is in range similar to that observed with other automated systems[9]. Similarly, cell counts performed at plating and before passaging on three successive passages of 11 iPSC lines maintained on the laboratory automation platform indicate that cell growth was similar between passages of the same lines and in the same order of magnitude across lines (FIG. 2N). This data thus demonstrates further the reliability of the laboratory automation to maintain iPSCs.

Figure 3:
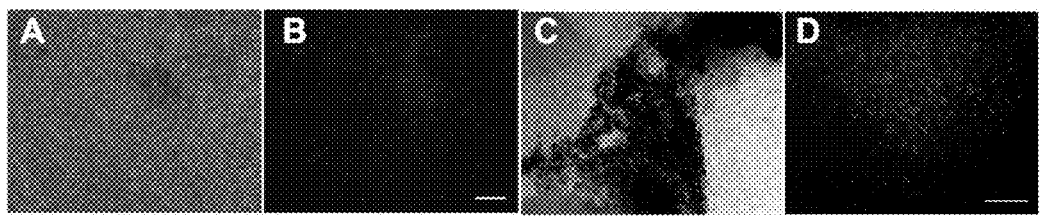
FIG. 3 shows retinal differentiation using the automated laboratory automation platform. (A, B) RGC differentiation. Representative bright field image (A) and corresponding fluorescence (B) of the reporter line BRN3B-mCherry A81-H7 following differentiation into RGCs at day 24. (C, D) RPE cell differentiation. Representative bright field (C) and fluorescent (D) images of H9 following differentiation to RPE cells at day 35 showing clear pigmentation and cobblestone morphology (C) and immunostained for the RPE marker PMEL with DAPI counterstain (D) characteristic of the RPE cells. Scale bars: 100 µm.

Example 4: Differentiation of PSCs into Retinal Cells on the Laboratory Automation Platform In order to assess the potential of this laboratory automation platform for long-term differentiation culture, the differentiation of human PSCs was directed towards two retinal lineages, RPE cells and RGCs, using protocols previously established[18-19]. Given the proof-of-concept nature and aim to ensure feasibility of long term differentiation no quantification was undertaken. The reporter line BRN3B-mCherry H7 16 was used for the RGC differentiation assay as this line fluoresces with expression of the specific RGC marker BRN3B, allowing for the screening of successful RGC differentiation. To make the RGC differentiation protocol described by Gill et al.[18] suitable for automation, it was slightly modified by replacing the initial embryoid body step with a monolayer differentiating culture. The protocol was followed as previously described. As shown in FIG. 3A-B, expression of mCherry in the differentiated culture was observed, indicating successful RGC differentiation using the laboratory automation platform of the present invention.

Next, RPE differentiation was performed using the laboratory automation platform.

The differentiation of cells into RPE cells is evident by the characteristic morphology and pigmentation of RPE cells. Differentiation of human PSCs plated in feeder-free conditions was directed into RPE cells using IGF1, DKK-1, noggin and bFGF as described in Lidgerwood, G. E.; Lim, S. Y.; Crombie, D. E., et al., (2016)[19]. Medium was changed every other day. Pigmented cells started appearing approximately four weeks later. The polygonal geometry of the RPE cells and expression of the RPE marker PMEL (FIG. 3C, D) was confirmed. Further enrichment would then be necessary to obtain purer population of cells of interest, by dissection or sorting of cells of interest as we previously described[18-19]. Together, these results provide proof-of-concept that automation can be utilised to facilitate stem cell maintenance and retinal differentiation. Importantly, no contamination was observed during the differentiation procedure, demonstrating the robustness of the laboratory automation platform for long-term sterile cell culture. The workflow for all procedures and potential applications is presented in FIG. 4.

The present invention describes the use of a modular laboratory automation platform to maintain, passage and differentiate human iPSCs. All protocols were adapted to automation using a feeder-free system for maintenance and differentiation. Some aspects of the work were performed offline, notably the reprogramming of cells and selection of successfully generated iPSCs. Further optimisation could allow these steps to be performed online, by integration within the modular laboratory automation platform, as done by others[9]. The automated system allows for substantial customization of both equipment and cell handling parameters providing the flexibility needed for cell culture of various cell types.

To reduce the risk of cross contamination, each line was cultivated within its own 6-well tissue culture plate. This format has the advantage of allowing for selections of cells for multiple applications, such as multiple long-term differentiation in various wells, or harvesting of samples for genomics, proteomics or lipidomics.

Importantly, there has been no contamination using this automated system, demonstrating the sterility of the system.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as broadly described herein.

REFERENCES

1. Park, I. H.; Zhao, R.; West, J. A., et al., Reprogramming of human somatic cells to pluripotency with defined factors. *Nature* 2008, 451 (7175), 141-6.
2. Takahashi, K.; Tanabe, K.; Ohnuki, M., et al., Induction of pluripotent stem cells from adult human fibroblasts by defined factors. *Cell* 2007, 131 (5), 861-72.
3. Yu, J.; Vodyanik, M. A.; Smuga-Otto, K., et al., Induced pluripotent stem cell lines derived from human somatic cells. *Science* 2007, 318 (5858), 1917-20.
4. Thomas, R. J.; Chandra, A.; Hourd, P. C., et al., Cell Culture Automation and Quality Engineering: A Necessary Partnership to Develop Optimized Manufacturing Processes for Cell-Based Therapies. *Journal of the Association for Laboratory Automation* 2008, 13 (3), 152-158.
5. Thomas, R. J.; Hourd, P. C.; Williams, D. J., Application of process quality engineering techniques to improve the understanding of the in vitro processing of stem cells for therapeutic use. *J Biotechnol* 2008, 136 (3-4), 148-55.
6. Kami, D.; Watakabe, K.; Yamazaki-Inoue, M., et al., Large-scale cell production of stem cells for clinical application using the automated cell processing machine. *BMC biotechnology* 2013, 13, 102.
7. Reichen, M.; Veraitch, F. S.; Szita, N., Development of a multiplexed microfluidic platform for the automated cultivation of embryonic stem cells. *J Lab Autom* 2013, 18 (6), 519-29.
8. Hussain, W.; Moens, N.; Veraitch, F. S., et al., Reproducible culture and differentiation of mouse embryonic stem cells using an automated microwell platform. *Biochem Eng J* 2013, 77 (100), 246-257.
9. Paull, D.; Sevilla, A.; Zhou, H., et al., Automated, high-throughput derivation, characterization and differentiation of induced pluripotent stem cells. *Nat Methods* 2015, 12 (9), 885-92.
10. Konagaya, S.; Ando, T.; Yamauchi, T., et al., Long-term maintenance of human induced pluripotent stem cells by automated cell culture system. *Sci Rep* 2015, 5, 16647.
11. Conway, M. K.; Gerger, M. J.; Balay, E. E., et al., Scalable 96-well Plate Based iPSC Culture and Production Using a Robotic Liquid Handling System. *J Vis Exp* 2015, (99), e52755.
12. McCaughey, T.; Liang, H. H.; Chen, C., et al., An Interactive Multimedia Approach to Improving Informed Consent for Induced Pluripotent Stem Cell Research. *Cell Stem Cell* 2016, 18 (3), 307-8.
13. Hung, S. S.; Van Bergen, N. J.; Jackson, S., et al., Study of mitochondrial respiratory defects on reprogramming to human induced pluripotent stem cells. *Aging* (Albany N.Y.) 2016.
14. Okita, K.; Matsumura, Y.; Sato, Y., et al., A more efficient method to generate integration-free human iPS cells. *Nature methods* 2011, 8 (5), 409-12.
15. Hernandez, D.; Millard, R.; Sivakumaran, P., et al., Electrical Stimulation Promotes Cardiac Differentiation of Human Induced Pluripotent Stem Cells. *Stem Cells Int* 2016, 2016, 1718041.
16. Sluch, V. M.; Davis, C.-h. O.; Ranganathan, V., et al., Differentiation of human ESCs to retinal ganglion cells using a CRISPR engineered reporter cell line. *Scientific Reports* 2015, 5, 16595.
17. Lamba, D. A.; Karl, M. O.; Ware, C. B., et al., Efficient generation of retinal progenitor cells from human embryonic stem cells. *Proc Natl Acad Sci USA* 2006, 103 (34), 12769-74.
18. Gill, K. P.; Hung, S. S.; Sharov, A., et al., Enriched retinal ganglion cells derived from human embryonic stem cells. *Sci Rep* 2016, 6, 30552.
19. Lidgerwood, G. E.; Lim, S. Y.; Crombie, D. E., et al., Defined Medium Conditions for the Induction and Expansion of Human Pluripotent Stem Cell-Derived Retinal Pigment Epithelium. *Stem Cell Rev* 2016, 12 (2), 179-88.
20. Chan, E. M.; Ratanasirintrawoot, S.; Park, I. H., et al., Live cell imaging distinguishes bona fide human iPS cells from partially reprogrammed cells. *Nat Biotechnol* 2009, 27 (11), 1033-7.
21. Willmann, C. A.; Hemeda, H.; Pieper, L. A., et al., To clone or not to clone? Induced pluripotent stem cells can be generated in bulk culture. *PLoS One* 2013, 8 (5), e65324.

The claims defining the invention are as follows:

1. An automated instrument for sterile cell culture, said instrument comprising:
    a platform for receiving and moving a cell culture plate from a housing;
    a manipulator arm for moving the culture plate between the housing and the platform and placing the culture plate on the platform;
    a receptacle containing a sterile solution to be dispensed controllably and sterilely to the culture plate;
    a disposable tip carrier carrying sterile disposable tips having a capacity of 5 mL for dispensing the sterile solution from the receptacle to the culture plate and removing solution from the culture plate;
    a liquid handling system including a robotic arm which interacts with the disposable tip carrier to fetch one or more disposable tips, and a syringe pump which is controlled to aliquot a first predetermined volume of the sterile solution from the receptacle into the one or more disposable tips, and to dispense the first predetermined volume of the sterile solution to and remove a second predetermined volume of solution from the culture plate such that the solution is sterilely dispensed from the disposable tips without dispersion outside the sterile cell culture while preventing contamination from the syringe pump, and wherein the syringe pump has at least 5 mL capacity and is controlled to remove the second predetermined volume of solution from the culture plate without causing additional air displacement in the disposable tip; and
    a controlling system configured to control the operation of each of the manipulator arm, the platform and the liquid handling system such that the liquid handling system controllably and sterilely dispenses and removes individual predetermined volumes of solution to and from the culture plate before the manipulator arm optionally returns the culture plate to the housing, thereby achieving automated maintenance, within the instrument, of cells in the cell culture.

2. An automated instrument according to claim 1 wherein the housing is an incubator for housing a culture plate comprising a cell culture well containing the cells or a hotel to hold the culture plate for later use.

3. An automated instrument according to claim 1 wherein said housing is an incubator or a hotel to which the manipulator arm has access to obtain or return the culture plate.

4. An automated instrument according to claim 1 wherein the receptacle contains a solution selected from a culture medium, PBS, cell releasing solution for dislodging cells or a coating for cell culture plates.

5. An automated instrument according to claim 1 wherein the platform is moveable.

6. An automated instrument according to claim 5 wherein the platform is moveable by tilting, shaking, rotating or any combination thereof.

7. An automated instrument according to claim 6 wherein the controlling system is programmed to tilt the platform at a predetermined angle for a predetermined number of times sufficient to spread the solution over the cells in culture.

8. An automated instrument according to claim 7 wherein the controlling system is programmed to tilt the platform for approximately 4 times at ±40° at each addition of solution.

9. An automated instrument according to claim 1 wherein the platform, one or more receptacles containing solution and disposable tip carrier are housed in a biosafety cabinet of the instrument.

10. An automated instrument according to claim 9 wherein the biosafety cabinet further includes the liquid handling system and the manipulator arm.

11. An automated instrument according to claim 1 wherein the disposable tips are filtered disposable tips.

12. An automated instrument according to claim 1 where the second predetermined volume is less than the first predetermined volume such that the liquid handling system removes a volume less than a volume present in the culture plate prior to delivering a volume of solution to the culture plate suitable to maintain the cells in cell culture.

13. An automated instrument according to claim 1 for sterile passaging of cells, wherein said sterile solution is a cell releasing solution.

14. An automated instrument for sterile passaging of cells according to claim 13, said system further including:
    a dispenser for controllably and sterilely dispensing a cell releasing solution to the cells in the culture plate.

15. An automated instrument for sterile passaging of cells according to claim 13 wherein the controlling system is configured to cause the liquid handling system to collect the cells from the culture plate for passaging to another culture plate and wherein a separate disposable tip is assigned for each culture plate for collection of cells and passage of cells.

16. An automated instrument for sterile passaging of cells according to claim 13 wherein the controlling system is configured to cause the liquid handling system to dispense the cell releasing solution to the culture plate for incubation with the cells for a predetermined time that is sufficient to detach the cells.

17. An automated instrument for sterile passaging of cells according to claim 13 wherein the controlling system is programmed to tilt the platform at a predetermined angle for a predetermined number of times sufficient to spread the cell releasing solution over the cell culture.

18. An automated instrument for sterile passaging of cells according to claim 13 wherein the controlling system is programmed to tilt the platform for approximately 20 times at ±10° to rinse the cells.

19. An automated instrument for sterile passaging of cells according to claim 13 wherein the controlling system is programmed to tilt the platform for approximately 20 times at ±10° with the cell releasing solution exposed to the cells.

20. An automated instrument for sterile passaging of cells according to claim 13 wherein the controlling system is programmed to tilt the platform for approximately 4 times at ±40° to change medium.

21. An automated instrument for sterile passaging of cells according to claim 13 wherein the controlling system is programmed to tilt the platform to shake for approximately 100 times ±5°; approximately 20 times ±40°, and then approximately 1000 times ±0.5° to detach the cells.

22. An automated instrument for sterile passaging of cells according to claim 13 wherein the controlling system is programmed to tilt the platform at an approximately 52° angle to aspirate and collect the cells following detachment from the culture plate for further passaging.

23. An automated instrument for sterile passaging of cells according to claim 13 wherein a split ratio for each culture plate for passaging cells is determined from a density of released cells following detachment from the culture plate.

24. An automated instrument for sterile passaging of cells according to claim 23 wherein the split ratio is in the range of approximately 1:1 to 1:6.

25. An automated instrument according to claim 1 for sterile differentiation of cells, wherein the sterile solution comprises a differentiation factor.

26. An automated instrument for sterile differentiation of cells, said system comprising an automated instrument according to claim 25 and further comprising:
    a differentiation unit for sterilely dispensing a differentiation factor to the cells in the culture plate to induce differentiation of the cells and wherein the liquid handling system further interacts with the differentiation unit and the controlling unit further automates the differentiation unit.

27. An automated instrument for sterile differentiating of cells according to claim 25 wherein the differentiation factor is a mixture of factors.

28. An automated instrument for sterile differentiating of cells according to claim 25 further including a cell sorting unit for identifying differentiated cells.

29. An automated instrument according to claim 1 wherein the cells are somatic cells or reprogrammed somatic cells.

30. An automated instrument according to claim 1 wherein the cells are iPSCs.

31. An automated instrument according to claim 1 wherein the somatic cells are fibroblasts.

32. An automated instrument according to claim 1 wherein the culture plates are modified to support stem cell growth and differentiation.

33. An automated instrument according to claim 32 wherein the culture plates are coated with matrices and peptides that support stem cell growth and differentiation.

34. An automated instrument according to claim 32 wherein the culture plates are coated with vitronectin, laminin, matrigel or feeder layers.

35. An automated method for sterile cell culture, said method comprising culturing cells in an automated instrument according to claim 1, wherein the controlling system automatically signals the manipulation arm to move a culture plate from the housing to the platform to receive a solution that is dispensed via the liquid handling system through a disposable tip such that the solution is dispensed controllably and sterilely without dispersion or removed accurately from the culture plate.

36. An automated method according to claim 35 wherein the cells are somatic cells, or reprogrammed somatic cells.

37. An automated method according to claim 35 wherein the cells are iPSCs.

38. An automated method according to claim 35 wherein the somatic cells are fibroblasts.

39. An automated method according to claim 35 wherein the culture plates are modified to support stem cell growth and differentiation.

40. An automated method according to claim 35 wherein the culture plates are coated with matrices and peptides that support stem cell growth and differentiation.

41. An automated method according to claim 35 wherein the culture plates are coated with vitronectin, laminin, matrigel or feeder layers.

42. An automated method for sterile passaging of cells said method comprising passaging cells in an automated instrument according to claim 1, wherein the controlling system automatically signals the manipulation arm to move a culture plate from the housing to the platform to receive a cell releasing solution that is dispensed via the liquid handling system through a disposable tip such that the cell releasing solution is dispensed controllably and sterilely without dispersion and the cells allowed to detach from the culture plate prior to being removed accurately from the culture plate for further passaging.

43. An automated method for sterile differentiating of cells, said method comprising differentiating cells in an automated instrument according to claim 1, wherein the controlling system automatically signals the manipulation arm to move a culture plate from the housing to the platform to receive a differentiation factor that is dispensed via the liquid handling system through a disposable tip such that the differentiation factor is dispensed controllably and sterilely without dispersion; and the culture plate returned to the housing for cell differentiation.

44. An automated instrument according to claim 1, wherein the liquid handling system interacts with the disposable tip carrier to fetch multiple disposable tips, and dispenses solution to multiple culture plates substantially simultaneously.

* * * * *